(12) United States Patent
Inoue et al.

(10) Patent No.: US 6,412,333 B2
(45) Date of Patent: Jul. 2, 2002

(54) EXHAUST GAS ANALYZING SYSTEM

(75) Inventors: Kaori Inoue; Masayuki Adachi, both of Kyoto (JP)

(73) Assignee: Horiba, Ltd., Koyto (JP)

( * ) Notice: Subject to any disclaimer, the term of this patent is extended or adjusted under 35 U.S.C. 154(b) by 0 days.

(21) Appl. No.: 09/729,474

(22) Filed: Dec. 4, 2000

(30) Foreign Application Priority Data

Dec. 6, 1999 (JP) ............................................ 11-345854

(51) Int. Cl.[7] .............................................. G01N 19/10
(52) U.S. Cl. ...................................................... 73/23.2
(58) Field of Search .......................................... 73/23.2

(56) References Cited

U.S. PATENT DOCUMENTS

| | | | | |
|---|---|---|---|---|
| 3,819,330 A | * | 6/1974 | Creighton ................. | 23/254 E |
| 3,833,016 A | * | 9/1974 | Lucero et al. .............. | 137/340 |
| 5,243,847 A | * | 9/1993 | Engeljehringer et al. ........ | 73/3 |
| 5,311,762 A | * | 5/1994 | Drexel ............................. | 73/3 |
| 5,394,730 A | * | 3/1995 | Crozier et al. ............... | 73/1 G |
| 5,410,907 A | * | 5/1995 | Ström et al. ............... | 73/23.31 |
| 5,450,749 A | * | 9/1995 | Ström et al. ............... | 73/117.3 |
| 5,569,838 A | * | 10/1996 | Broedel et al. ............ | 73/23.31 |
| 5,807,750 A | * | 9/1998 | Baum et al. ................ | 436/164 |
| 5,821,435 A | * | 10/1998 | Kojima ..................... | 73/863.01 |
| 6,062,092 A | * | 5/2000 | Weaver .................... | 73/863.03 |

* cited by examiner

*Primary Examiner*—Hezron Williams
*Assistant Examiner*—David J. Wiggins
(74) *Attorney, Agent, or Firm*—Oppenheimer Wolff & Donnelly LLP

(57) ABSTRACT

The present invention provides an exhaust gas analyzing system utilizing a mini-diluter method in which measurement accuracy of the exhaust gas analyzing system can be evaluated by the system itself. In the exhaust gas analyzing system, a sampling flow path is connected to an exhaust gas flow path through which gas exhausted from an engine flows to sample a portion of the exhaust gas. The sampled exhaust gas is diluted with dilution gas introduced through a dilution gas flow path which is connected in parallel to the sampling flow path. A portion of the diluted exhaust gas is stored in a sample bag. The diluted exhaust gas in the sample bag is analyzed in a gas analyzing portion, wherein flow rate of the exhaust gas is measured, trace gas with a known concentration is introduced into the exhaust gas flow path upstream from a connecting point located between the exhaust gas flow path and the sampling flow path while monitoring flow rate of the trace gas, diluted trace gas is analyzed in the gas analyzing portion, and total mass of the trace gas calculated from a result of the analysis is compared with total mass of the introduced trace gas to evaluate measurement itself.

18 Claims, 3 Drawing Sheets

EXHAUST GAS ANALYZING SYSTEM

FIELD OF THE INVENTION

The present invention relates to an exhaust gas analyzing system.

DESCRIPTION OF THE PRIOR ART

Currently, a CVS method (Constant Volume Sampling) is widely used as a sampling method to measure mass of components in gas exhausted from an engine of an automobile. A possibility of insufficient accuracy is pointed out in measuring exhaust gas of a ULEV (Ultra Low Emission Vehicle), a SULEV (Super Ultra Low Emission Vehicle), and like when the CVS method is used.

A substitute for the above CVS method is a mini-diluter method. In the mini-diluter method, a portion of the exhaust gas is sampled instead of diluting the entire quantity of exhaust gas from the engine. The sampled exhaust gas is diluted at a certain dilution ratio, the diluted sample gas is gathered in a sample bag by an amount proportional to a flow rate of the exhaust gas from the engine, and the diluted sample gas in the sample bag is analyzed.

FIG. 3 schematically shows an example of an exhaust gas analyzing system for which the mini-diluter method is used. Reference numeral 1 represents an engine of an automobile, reference numeral 2 represents an exhaust gas flow path connected to an exhaust pipe connected to the engine 1, and reference numeral 3 represents a flowmeter (digital flowmeter, for example) for measuring a flow rate of the entire exhaust gas G flowing through the exhaust gas flow path 2. Reference numeral 4 represents a sampling flow path that is connected to the exhaust gas flow path 2 at a point 5 downstream from the flowmeter 3. A portion of the exhaust gas G, which is sample gas S, flows through the sampling flow path 4.

Reference numeral 6 represents a mini-diluter which is coupled to the sampling flow path 4. Reference numeral 4A represents a sampling flow path in the mini-diluter 6 in which a CFV (critical flow venturi) 7 for defining flow rate of the sample gas S flowing through the sampling flow path 4A and a suction pump 8 are provided. Reference numeral 9 represents a dilution gas flow path provided in parallel with the sampling flow path 4A. A pressure controller 10 and a CFV 11 is provided in the dilution flow path for defining a flow rate of the dilution gas D. A downstream side of the CFV 11 is connected to the CFV 7 by the sampling flow path 4A at a point 12 which is between the CFV 7 and the pump 8. The pressure controller 10 equalizes pressure on an inlet side of the CFV 7 of the flow path 4A with pressure on an inlet side of the CFV 11 of the dilution gas flow path 9. A cylinder 13 containing dilution gas (e.g., nitrogen gas) is provided upstream of the pressure controller 10 (more specifically, outside the mini-diluter 6).

Sampling flow path 4A includes a sample bag 16 which is provided downstream from the suction pump 8. A mass-flow controller 14 (MFC) includes a flow rate measuring portion and a flow rate control valve. The mass-flow controller 14 measures and controls the flow rate via a three-way solenoid valve 15 as a selector valve. Reference numeral 17 represents an overflow flow path, and the overflow path 17 is connected to a point 18 between the suction pump 8 of the sampling flow path 4 and the mass-flow controller 14.

Reference numeral 19 represents a gas analyzing portion provided in a rear stage of the mini-diluter 6, and a plurality of gas analyzers 19a to 19n, for example, are provided in parallel with each other in a flow path 20. The flow path 20 is connected to the three-way solenoid valve 15. Exemplary gas analyzers 19a to 19n are NDIR (non-dispersive infrared analyzer) for measuring CO and $CO_2$, CLD (chemiluminescent analyzer) for measuring $NO_x$, FID (flame ionization detector) for measuring THC (total hydrocarbon), and the like.

Furthermore, reference numeral 21 represents an arithmetic controller having a personal computer, for example. The arithmetic controller performs computations based on output signals from the flowmeter 3, mass-flow controller 14, and gas analyzing portion 19 and controls the entire exhaust gas analyzing system based on a result of the computations.

For the exhaust gas analyzing system having the above structure and for which the mini-diluter method is used, the exhaust gas analysis is carried out as follows. Flow rate of the exhaust gas G from the engine 1 is measured by the flowmeter 3 and output from the flowmeter 3 is input into the arithmetic controller 21. Because the suction pump 8 in the mini-diluter 6 is operating, a portion of the exhaust gas G, wherein a flow rate has been measured, is taken in the sampling flow path 4 as the sample gas S. The sample gas S flows through the flow path 4A of the mini-diluter 6 toward the suction pump 8. By operation of the suction pump 8, the dilution gas D flows through the dilution gas flow path 9 provided in parallel with the flow path 4A.

In this case, because the dilution gas flow path 9 is provided with the pressure controller 10 which equalizes the pressure on the inlet side of the CFV 7 of the flow path 4A with the pressure on the inlet side of the CFV 11 of the dilution gas flow path 9 and because the flow path 4A and the dilution gas flow path 9 are respectively provided with the CFVs 7 and 11 for defining the flow rates of the gas S and D flowing through the flow paths, 4A and 9, ways of changing flow rates of the gas S and D flowing through both flow paths 4A and 9 are equalized with each other and a ratio between the flow rates is always constant. The gas flows S and D merge with each other at a confluence 12, and the sample gas S is diluted with the dilution gas D to a certain consistency.

The diluted sample gas S flows through the suction pump 8 to a downstream side of the pump 8, and a portion of the gas S flows toward the three-way solenoid valve 15. Flow rate of the portion of the gas S flowing towards the three-way solenoid valve is set by the mass-flow controller 14 provided in the flow path 4A. Because the three-way solenoid valve 15 allows the mass-flow controller 14 and the sample bag 16 to communicate with each other when the power is turned off, the diluted sample gas S which has passed through the mass-flow controller 14 is gathered in the sample bag 16. The remainder of the diluted sample gas S is exhausted through the overflow flow path 17.

An opening degree of the flow rate control valve of the mass-flow controller 14 is controlled actively such that the flow rate of the diluted sample gas S passing through the mass-flow controller 14 is proportional to a flow rate of the exhaust gas G flowing through the exhaust gas flow path 2. More specifically, because the flow rate of the exhaust gas is measured by the flowmeter 3 and the result of the measurement is input into the arithmetic controller 21 as described previously, the arithmetic controller 21 sends a control command to set the opening degree of the flow rate control valve of the mass-flow controller 14 at a predetermined value. Thus, the mass-flow controller 14 allows the sample gas S to flow at a proportional flow rate to the flow rate of the exhaust gas G.

When the predetermined sampling ends, power to the three-way solenoid valve 15 is turned on, the sample bag 16 and the flow path 20 communicate with each other, the diluted sample gas S taken into the sample bag 16 is supplied to the gas analyzing portion 19, and concentrations of components to be measured contained in the diluted sample gas S (e.g., CO, $CO_2$, $NO_x$, and THC) are respectively measured by NDIR, CLD, FID, and the like.

In this case, mass $M_x$ of a component X before dilution is given by the following expression (1).

$$M_x = C_{xbag} \times V_{ex} \times R \times \rho_x \quad (1)$$

Where $C_{xbag}$ represents a measured concentration of the component X in the bag, $V_{ex}$ represents total volume of the exhaust gas, $R_d$ represents dilution rate, $\rho_x$ density of the component X.

The mass $M_x$ of component X in the exhaust gas G before dilution can be easily obtained because the measured concentration $C_{xbag}$ of the component X in the bag, the total flow rate $V_{ex}$ of the exhaust gas, the dilution rate $R_d$, and the density $\rho_x$ of the component X are respectively known. According to the exhaust gas analyzing system for which the mini-diluter method is used, the mass of the low-concentration exhaust gas component can be accurately measured.

However, in the exhaust gas analyzing system for which the mini-diluter method is used, it is essential to measure the flow rate of the exhaust gas G in real time, and a large error may be incorporated into the finally obtained mass of the component in the exhaust gas because it depends on the measurement error of the flow rate.

The present invention has been accomplished with the above circumstances in view, and it is an object of the present invention to provide an exhaust gas analyzer in which measurement accuracy of the exhaust gas analyzing system utilizing a mini-diluter method can be evaluated by the system itself.

SUMMARY OF THE INVENTION

To achieve the above object, in accordance with the present invention, an exhaust gas analyzing system is provided. The exhaust gas analyzing system comprises a sampling flow path connected to an exhaust gas flow path through which gas exhausted from an engine flows to sample a part of the exhaust gas. The sampled exhaust gas is diluted with dilution gas introduced through a dilution gas flow path connected in parallel to the sampling flow path. A portion of the diluted exhaust gas is stored in a sample bag. The diluted exhaust gas in the sample bag is analyzed in a gas analyzing portion, wherein flow rate of the exhaust gas is measured, trace gas with a known concentration is introduced into the exhaust gas flow path on an upstream side from a connecting point between the exhaust gas flow path and the sampling flow path while monitoring flow rate of the trace gas. The diluted trace gas is analyzed in the gas analyzing portion, and total mass of the trace gas calculated from a result of the analysis is compared with total mass of the introduced trace gas to evaluate measurement itself.

In the exhaust gas analyzing system, the total mass of the trace gas introduced into the exhaust gas flow is known. It is possible to evaluate accuracy of the measurement itself by comparing the total mass of the measured and calculated trace gas (using the mini-diluter method) with the above known total mass. As a result, reliability of the exhaust gas analyzing system for which the mini-diluter method is used and which includes measurement of the flow rate of the exhaust gas is improved.

DETAILED DESCRIPTION OF THE PREFERRED EMBODIMENTS

Figure 1:
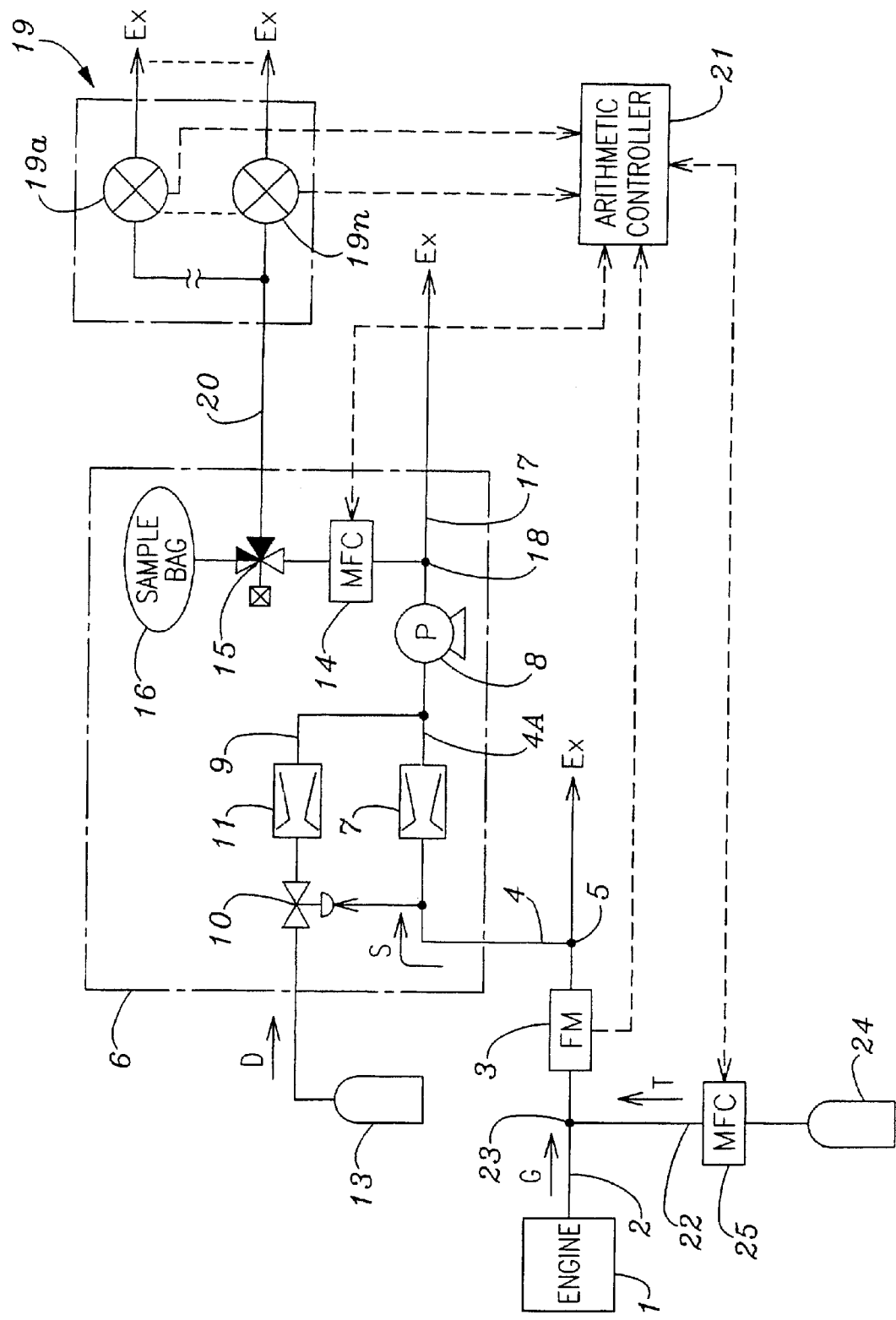
FIG. 1 schematically shows an example of a structure of an exhaust gas analyzing system of the present invention.

Embodiments of the present invention will be described by reference to the drawings. FIG. 1 shows a first embodiment of an exhaust gas analyzing system of the present invention. The exhaust gas analyzing system is significantly different from the prior-art exhaust gas analyzing system in that proper trace gas T with a known concentration and a known flow rate is introduced upstream from a point 5 that is for sampling gas from an exhaust gas flow path 2 into a mini-diluter 6, diluted trace gas T is analyzed by a trace gas analyzer provided in a gas analyzing portion 19, and total mass of the trace gas T calculated from a result of the analysis is compared with total mass of the above introduced trace gas T to evaluate measurement itself.

In FIG. 1, reference numeral 22 represents a trace gas introducing path for introducing the trace gas T into the exhaust gas flow path 2. Trace gas introducing path 22 is connected to the exhaust gas flow path 2 at a point 23. A cylinder 24 of He (helium gas), which is the trace gas T and a mass-flow controller 25 for measuring and controlling flow rate of the trace gas T are provided upstream of the trace introducing path 22. The mass-flow controller 25 is controlled by an arithmetic controller 21, and the mass-flow controller 25 outputs a detected flow rate measurement to the arithmetic controller 21.

In addition to NDIR, CLD, and FID for measuring concentrations of CO, $CO_2$, $NO_x$, and THC, the gas analyzing portion 19 is provided with a mass spectrometer to analyze the concentration of the gas (trace gas).

In the exhaust gas analyzing system with the above structure, the exhaust gas G from the engine 1 flows through the exhaust gas flow path 2 and is mixed with the trace gas T introduced into the exhaust gas flow path 2 through the trace gas introducing path 22. The flow rate of the trace gas T is controlled to a constant value by the mass-flow controller 25 disposed in the trace gas introducing path 22. The flow rate at this time is monitored by the arithmetic controller 21.

The exhaust gas G and the trace gas T pass through the flowmeter 3 and a portion of the exhaust gas G and trace gas T flows into the sampling flow path 4 and the remainder is exhausted. Output from the flowmeter 3 is sent to the arithmetic controller 21.

Figure 3:
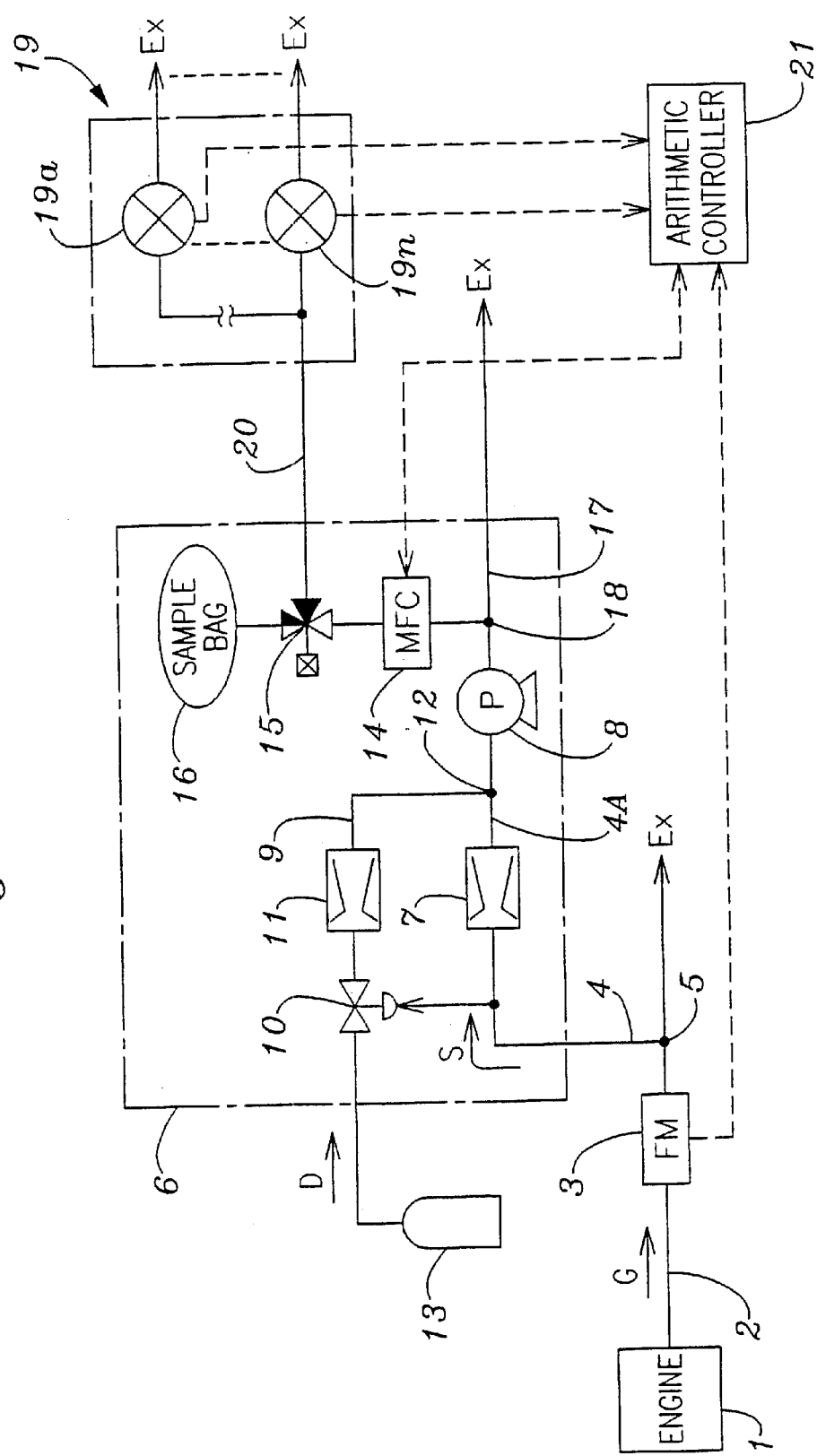
FIG. 3 schematically shows an example of a structure of an exhaust gas analyzing system for which a mini-diluter method is used.

The sample gas S and the trace gas T that have flowed into the sampling flow path 4 are diluted with dilution gas D in the mini-diluter 6 and concentrations (concentrations in the bag) of respective components after dilution are obtained by NDIR, CLD, FID, the mass spectrometer, and the like in the gas analyzing portion 19 similarly to the exhaust gas analyzing system shown in FIG. 3. In this case, mass of the respective components (and also the trace gas T) can be also obtained by the above expression (1).

On the other hand, mass $M_t$ of the trace gas T introduced into the exhaust gas flow path 2 through the trace gas introducing path 22 is given by the following expression (2).

$$M_t = C_t \times V_t \times \rho_t \qquad (2)$$

Where $C_t$ represents a concentration of the trace gas T in introduction, $V_t$ represents total introduced volume of the trace gas T, and $\rho_t$ represents density of the trace gas T.

In theory, $M_x$ given by the expression (1) and $M_t$ given by the expression (2) should be the same value with respect to the trace gas T. Because $M_t$ can be obtained relatively accurately, a difference between $M_x$ and $M_t$ can be regarded as an indicator of correctness of the gas analysis for which the mini-diluter 6 is used.

In accordance with the exhaust gas analyzing system described above, the total mass of the trace gas T introduced into the exhaust gas G is known. By comparing the total mass of the trace gas T measured and calculated by using the mini-diluter method with the above known total mass, it is possible to evaluate accuracy of the measurement itself. As a result, reliability of the exhaust gas analyzing system for which the mini-diluter method is used and which includes measurement of the flow rate of the exhaust gas is improved.

Figure 2:
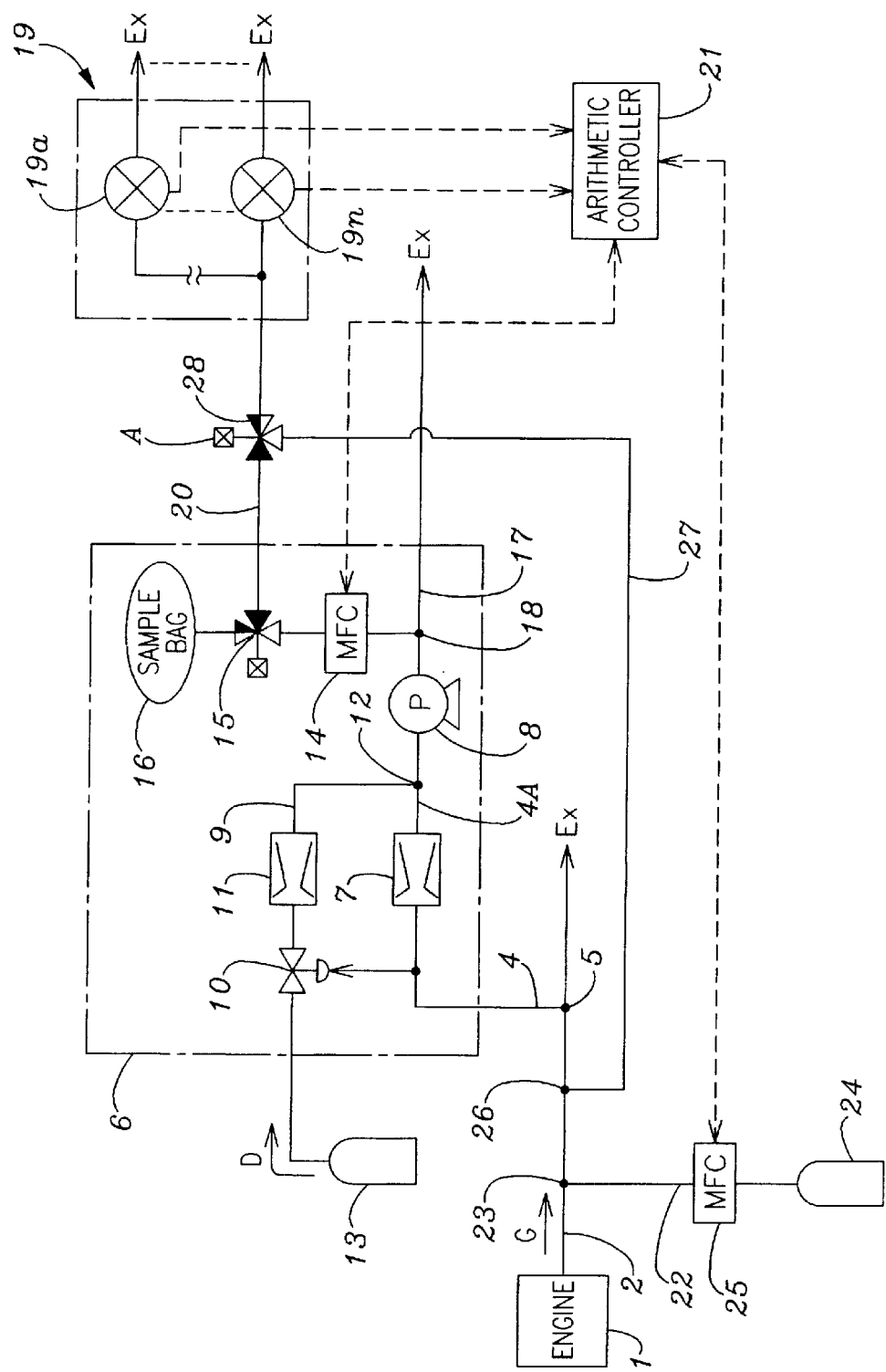
FIG. 2 schematically shows another example of the structure of the exhaust gas analyzing system of the present invention.

FIG. 2 shows a second embodiment of the present invention. In this embodiment, flow rate of gas (mixture of exhaust gas G and trace gas T) flowing through the exhaust gas flow path 2 is measured from change from a concentration of the trace gas T before mixing to the concentration after mixing. The flowmeter 3 is removed from the exhaust gas flow path 2, one end of a flow path 27 is connected to a point 26 between a connecting point 23 and a connecting point 5 of the exhaust gas flow path 2, and the other end of the flow path 27 is connected to a three-way solenoid valve 28 provided in a flow path 20.

In the structure shown in FIG. 2, sampling into the sample bag 16 is carried out while the concentration of the trace gas T in gas sampled from the connecting point 26 is measured in the gas analyzing portion 19. Flow rate of the exhaust gas G is calculated from the concentration of the trace gas after mixing in real time and fed back to the sampling flow rate into the sample bag 16. After sampling into the sample bag 16 is completed, it is possible to evaluate measurement accuracy similarly to the above first embodiment by analyzing components (including the trace gas T) in diluted gas obtained by the sampling. In other words, because the trace gas T is used for measuring the flow rate of the exhaust gas G in the embodiment shown in FIG. 2, it is possible to omit the flowmeter which measures the flow rate of the exhaust gas G.

The present invention is not limited to the above respective embodiments. For example, other chemically stable components such as $SF_6$ can be used as the trace gas T. When $SF_6$ is used as the trace gas T, an FTIR method gas analyzer using Fourier transform infrared spectrophotometer, for example, can be used to analyze the concentration of $SF_6$ as an alternative to NDIR. Only by the FTIR method gas analyzer, CO, $CO_2$, NO, and $H_2O$ (which are main components of the engine exhaust) and $NO_2$, $N_2O$, $NH_3$, HCHO, and $CH_4$ (which are of great interest) can be measured simultaneously. Furthermore, the structure of the gas analyzing portion 19 can be simplified.

The structure for defining the flow path in the mini-diluter 6 is not limited to the CFV, and a flow rate controller such as mass flow controller can be used.

As described above, in the exhaust gas analyzing system of the present invention, because measurement accuracy of the exhaust gas analyzing system utilizing the mini-diluter method can be evaluated by the system itself, reliability of the exhaust gas analyzing system utilizing the mini-diluter method and which includes measurement of the flow rate of the exhaust gas can be improved.

What is claimed is:

1. An exhaust gas analyzing system, comprising:
    a sampling flow path connected to an exhaust gas flow path through which gas exhausted from an engine flows to sample a portion of said exhaust gas;
    a dilution gas flow path connected in parallel to said sampling flow path, said dilution gas flow path diluting said sampled exhaust gas with a dilution gas to form a diluted exhaust gas;
    a sample bag storing a portion of said diluted exhaust gas;
    a gas analyzing portion analyzing said diluted exhaust gas in said sample bag;
        wherein flow rate of said exhaust gas is measured; and
        a trace gas with a known concentration introduced into said exhaust flow path while monitoring flow rate of said trace gas, said trace gas introduced into said exhaust flow, path upstream from a first connecting point, said first connecting point connecting said exhaust gas flow path to said sampling flow path, said trace gas forming diluted trace gas when mixed with said diluted exhaust gas and said dilution gas, said diluted trace gas analyzed in said gas analyzing portion;
        wherein total mass of said trace gas calculated from a result of said analysis in said gas analyzing portion is compared with total mass of said introduced trace gas to evaluate said analysis of said diluted trace gas in said gas analyzing portion.

2. The exhaust gas analyzing system of claim 1, further comprising:
    a mini-diluter connected to said sampling flow path, said mini-diluter comprising:
        a first critical flow venturi connected to said sampling flow path; and
        a second critical flow venturi connected to said dilution gas flow path.

3. The exhaust gas analyzing system of claim 2, further comprising a pressure controller connected to said dilution gas flow path, said pressure controller equalizing pressure on an inlet side of said first critical venturi with pressure on an inlet side of said second critical venturi.

4. The exhaust gas analyzing system of claim 3, further comprising:
    a suction pump located downstream of said first critical flow venturi and said second critical flow venturi;
        wherein said sample bag is located downstream of said suction pump.

5. The exhaust gas analyzing system of claim 4, further comprising:
    a mass-flow controller connected downstream of said suction pump; and
    a three-way solenoid valve located downstream of said mass-flow controller, said three-way solenoid valve located upstream of said sample bag.

6. The exhaust gas analyzing system of claim 5, further comprising:
    an overflow path connected at downstream of said suction pump and upstream of said mass-flow controller.

7. The exhaust gas analyzing system of claim 6, wherein said gas analyzing portion is located in a rear stage of said mini-diluter, said gas analyzing portion having a plurality of gas analyzers in parallel with each other in a flow path, and said flow path connected to said three-way solenoid valve.

8. The exhaust gas analyzing system of claim 7, wherein said plurality of gas analyzers are at least one of non-dispersive infrared analyzers, chemiluminescent analyzers, and flame ionization detectors.

9. The exhaust gas analyzing system of claim 8, wherein said non-dispersive infrared analyzers measure CO and $CO_2$, said chemiluminescent analyzers measure $NO_x$, and said flame ionization detectors measure total hydrocarbon.

10. The exhaust gas analyzing system of claim 9, further comprising:
   a flowmeter located upstream of said first connecting point;
   a trace gas introducing path connected to said exhaust gas flow path at a second connecting point, said second connecting point located upstream of said first connecting point;
   a trace gas source located upstream of said trace gas introducing path; and another mass-flow controller, said another mass-flow controller located downstream of said trace gas source, said another mass-flow controller measuring and controlling flow rate of said trace gas.

11. The exhaust gas analyzing system of claim 10, further comprising:
   an arithmetic controller, said arithmetic controller controlling said flowmeter, said mass-flow controller, and said another mass-flow controller.

12. The exhaust gas analyzing system of claim 11, wherein said arithmetic controller receives and output signal from said flowmeter.

13. The exhaust gas analyzing system of claim 12, wherein total mass of said trace gas calculated from a result of said analysis in said gas analyzing portion is given by $M_x = C_{xbag} \times V_{ex} \times R \times \rho_x$, and wherein total mass of said introduced trace gas is given by $M_t = C_t \times V_t \times \rho_t$.

14. The exhaust gas analyzing system of claim 9, further comprising:
   a trace gas introducing path connected to said exhaust gas flow path;
   a trace gas source located upstream of said trace gas introducing path; and
   another mass-flow controller, said another mass-flow controller located downstream of said trace gas source, said another mass-flow controller measuring and controlling flow rate of said trace gas;
   another three-way solenoid valve having a first valve, a second valve, and a third valve;
      said first valve of said another three-way solenoid valve coupled to said three-way solenoid valve;
      said second valve of said another three-way solenoid valve coupled to said exhaust gas flow path at a third connecting point located upstream of said first connecting point and downstream of said second connecting point; and
      said third valve of said another three-way solenoid valve coupled to said gas analyzing portion.

15. The exhaust gas analyzing system of claim 14, further comprising:
   an arithmetic controller, said arithmetic controller controlling said mass-flow controller and said another mass-flow controller.

16. The exhaust gas analyzing system of claim 1, wherein said trace gas is helium gas.

17. The exhaust gas analyzing system of claim 1, wherein said trace gas is $SF_6$.

18. The exhaust gas analyzing system of claim 1, wherein said trace gas concentration is monitored after mixing with said exhaust gas to determine flow rate of said exhaust gas for proportionally controlling flow rate of a mass flow controller to that of said exhaust gas.

* * * * *